United States Patent [19]

Selkirk et al.

[11] Patent Number: 4,973,591

[45] Date of Patent: Nov. 27, 1990

[54] PARENTERAL FORMULATIONS OF 1-DIPHENYLMETHYL-4-((2-(4-METHYL-PHENYL)-5-METHYL-1H-IMIDAZOL-4-YL)METHYL)PIPERAZINE

[75] Inventors: Alastair B. Selkirk, Edinburgh; Michael J. Dey, West Lothian, both of Scotland

[73] Assignee: Syntex Pharmaceuticals, Ltd., Maidenhead, England

[21] Appl. No.: 260,628

[22] Filed: Oct. 21, 1988

[51] Int. Cl.$^5$ .......................................... A61K 31/495
[52] U.S. Cl. .................................................. 514/255
[58] Field of Search ....................................... 514/255

[56] References Cited

U.S. PATENT DOCUMENTS

| | | | |
|---|---|---|---|
| 3,362,956 | 1/1968 | Archer | 260/268 |
| 3,491,098 | 1/1970 | Acher | 260/268 |
| 3,631,043 | 12/1971 | Regnier et al. | 260/250 A |
| 3,649,631 | 3/1972 | Koppe et al. | 260/268 H |
| 3,927,011 | 12/1975 | Nakanishi et al. | 260/296 R |
| 4,022,783 | 5/1977 | Shroff et al. | 260/268 H |
| 4,243,806 | 1/1981 | Raeymaekers et al. | 544/396 |
| 4,404,382 | 9/1983 | Gall | 544/360 |

FOREIGN PATENT DOCUMENTS

| | | |
|---|---|---|
| 0054974 | 6/1982 | European Pat. Off. . |
| 0072623 | 8/1983 | European Pat. Off. . |
| 2022073 | 5/1979 | United Kingdom . |
| 1551993 | 9/1979 | United Kingdom . |

*Primary Examiner*—Douglas W. Robinson
*Assistant Examiner*—Zohyeh A. Fay
*Attorney, Agent, or Firm*—David A. Lowin; Tom M. Moran

[57] ABSTRACT

A pharmaceutical formulation suitable for parenteral (preferably intravenous) adminstration includes an effective amount of 1-diphenylmethyl-4-[(2-(4-methylphenyl)-5-methyl-1H-imidazol-4-yl)methyl]piperazine and a suitable amount of an acid to generate a pharmaceutically acceptable salt having a pH above about 3.0 and a solubility above about 4.0 mg/ml. The intravenous formulation optionally includes a suitable tonicifier in a quantity sufficient to achieve isotonicity with body fluids. The salt is formed in situ during the formulation process. The slat of tartaric acid is preferred; suitable salts for lower concentration dosages are the citric acid and methane sulphonic acid salts.

17 Claims, No Drawings

PARENTERAL FORMULATIONS OF 1-DIPHENYLMETHYL-4-((2-(4-METHYL-PHENYL)-5-METHYL-1H-IMIDAZOL-4-YL)METHYL)PIPERAZINE

BACKGROUND OF THE INVENTION

Cross-reference to Related Applications

This application is related to U.S. Ser. No. 042,181, filed Apr. 24, 1987 now U.S. Pat. No. 4,829,065, and its continuation in part U.S. Ser. No. 07/260,969, filed contemporaneously herewith, both incorporated herein by reference, where preparation of the subject compound, 1-diphenylmethyl-(4-[(2-(4-methylphenyl)-5-methyl-1H-imidazol-4-yl)methyl]piperazine and its uses are taught.

Field of the Invention

The present invention relates to parenteral formulations of 1-diphenylmethyl-4-[(2-(4-methylphenyl)-5-methyl-1H-imidazol-4-yl)methyl]piperazine, particularly to intravenous formulations with the tartrate salt thereof. The invention is also directed to methods preparing the formulation, and to methods for treating mammals having any of a variety of disease states including:

diseases treated by direct neuronal protection, such as ischemia including focal and global ischemia, spinal injuries, head trauma, and neurological diseases such as Alzheimer's and Huntington's chorea;

diseases treated by inhibition of sodium ion such as uraemic and hyponatraemic encephalopathy; and diseases treated with calcium channel antagonists, including:

diseases treated by inhibiting cerebrovascular vasospasm and by cerebrovascular vasodilation, such as migraine, stroke vasospasm due to subarachnoid hemorrhage, epilepsy or epileptic psychotic symptoms, and cerebrovascular ischemia induced by cocaine abuse; and cardiovascular diseases, such as hypertension, angina, stable and unstable angina, Prinzmetal angina, arrhythmia, thrombosis, embolism, and congestive heart failure such as chronic or acute cardiac failure; and ischemia of lower legs due to peripheral vascular disease, e.g., intermittent claudication;

spasms of smooth muscle: such as the ureter, the bladder, uterine cramps, diuresis, and irritable bowel syndrome; and uses during surgery: such as bypass grafts, angiography, angioplasty, organ preservation during transplant, hypertensive crisis or post operative hypertension, by parenteral administration of a formulation of the invention.

Background Information

1-Diphenylmethyl-4-[(2-(4-methylphenyl)-5-methyl-1H-imidazol-4-yl)methyl]piperazine, is a potent calcium channel antagonist, having activity for treating a variety of disease states in mammals. It is often preferred to administer such active agents via the parenteral route. However, when initial attempts were made to prepare formulations suitable for intravenous administration, it was discovered that this compound exhibited significant solubility problems, particularly at physiological pH, both in the formulation process and upon administration to test animals.

It was, therefore, desired to develop a stable, soluble, physiologically and clinically acceptable solution of 1-diphenylmethyl-4-[(2-(4-methylphenyl)-5-methyl-1H-imidazol-4-yl)methyl]piperazine, suitable for administration by intravenous or other parenteral routes, and compatible with a wide variety of infusion fluids.

In animal testing with a 8 mg/ml solution of 1-diphenylmethyl-4-[(2-(4-methylphenyl)-5-methyl-1H-imidazol-4-yl)methyl]piperazine, trihydrochloride, adjusted to a pH of about 3-3.5 with sodium hydroxide, compound precipitation was observed in rat tail veins shortly after injection. This was evidenced by bruising of the vein, hardening of the tail and other signs of pain upon injection. This finding was verified by slowly dropping approximately 1 ml of the injectable formulation into 50 ml of 0.1M pH 7.4 phosphate buffer, whereupon a white precipitate was observed immediately at the interface between the two liquids.

Experiments with a variety of aqueous miscible cosolvents commonly used to improve the solubility of parenteral products [for example, various mixtures of polyethylene glycol (PEG 300), propylene glycol (PG) and ethanol], achieved limited increase in the solubility of the active agent. However, all of the resulting solutions showed excessive irritation upon tail vein injection in rats.

Other salts were investigated with the aim of producing adequate solubility at a physiologically acceptable pH and a reduction in irritancy upon administration. The aspartic, fumaric, phosphoric and gultamic acid salts showed only moderate changes in properties, and were quite difficult to prepare. Acetic, maleic, malonic, oxalic and succinic acid salts did not have adequate solubility. The ascorbic acid salt was also relatively insoluble, and solutions showed rapid discolouration upon standing. The sulfuric acid salt was tried, but rejected as physiologically unacceptable due to its low pH (1.76) in solution.

The citric and methane sulphonic acid salts were tested, showing better solubilities (in excess of about 4 mg/ml) but minor irritation upon tail vein injection. These formulations were outside the optimum pH range for physiological compatibility when prepared at the desired concentrations. The citrate and methane sulphonate salts are acceptable for lower concentrations than those optimally preferred for the present invention.

Surprisingly, it was discovered that only the tartrate salt of 1-diphenylmethyl-4-[(2-(4-methylphenyl)-5-methyl-1H-imidazol-4-yl)methyl]piperazine provides the full combination of properties desired in such a parenteral formulation. It gives a pH of greater than about 3.0, and has a solubility of greater than 4.0 mg/ml. The solution is physically and chemically stable over at least 12 months storage at 25° C. and is compatible with a wide range of commercially available infusion fluids. Acceptable irritancy levels were demonstrated over a one week tail vein injection trial, and successful administration to both rats and baboons has been demonstrated over 28 days.

SUMMARY OF THE INVENTION

One aspect of the present invention is a parenteral formulation of 1-diphenylmethyl-4-[(2-(4-methylphenyl)-5-methyl-1H-imidazol-4-yl)methyl]piperazine, tartaric acid, a tonicifier, and water.

In another aspect, the invention relates to a method of treating mammals having any of a variety of disease states including:

diseases treated by direct neuronal protection, such as ischemia including focal and global ischemia, spinal injuries, head trauma, and neurological diseases such as Alzheimer's and Huntington's chorea;

diseases treated by inhibition of sodium ion such as uraemic and hyponatraemic encephalopathy; and diseases treated with calcium channel antagonists, including:

diseases treated by inhibiting cerebrovascular vasospasm and by cerebrovascular vasodilation, such as migraine, stroke, vasospasm due to subarachnoid hemorrhage, epilepsy or epileptic psychotic symptoms, and cerebrovascular ischemia induced by cocaine abuse; and cardiovascular diseases, such as hypertension, angina, stable and unstable angina, Prinzmetal angina, arrhythmia, thrombosis, embolism, and congestive heart failure such as chronic or acute cardiac failure; and ischemia of lower legs due to peripheral vascular disease, e.g., intermittent claudication;

spasms of smooth muscle, such as the ureter, the bladder, uterine cramps, diuresis and irritable bowel syndrome; and uses during surgery: such as bypass grafts, angiography, angioplasty, organ preservation during transplant, hypertensive crisis or post operative hypertension, especially to a method for treating ischemia in a mammal, by parenteral (particularly intravenous) administration, to a mammal in need of such treatment, of a therapeutically effective amount of 1-diphenylmethyl-4-[(2-(4-methylphenyl)-5-methyl-1H -imidazol-4-yl)methyl]piperazine tartrate in a formulation suitable therefor.

Still another aspect of the present invention involves a method for preparing the formulations of the present invention by the in situ formation of a pharmaceutically acceptable salt having the desired pH and solubility characteristics for parenteral administration.

DETAILED DESCRIPTION OF THE INVENTION

Definitions and General Parameters

The following definitions are set forth to illustrate and define the meaning and scope of the various terms used to describe the invention herein.

1-Diphenylmethyl-4-[(2-(4-methylphenyl)-5-methyl-1H-imidazol-4-yl)methyl]piperazine has the following formula:

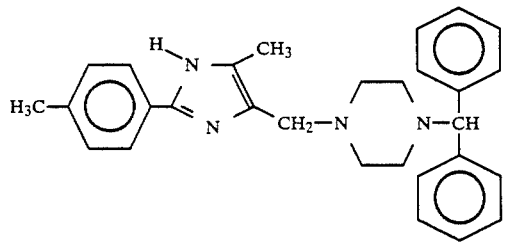

As used herein, the term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

As used herein, the term "q.s." means adding a quantity sufficient to achieve a stated function, e.g., to bring a solution to the desired volume (i.e., 100%).

As used herein the term "effective amount" means a dosage sufficient to provide treatment for the disease state being treated. This will vary depending on the patient, the disease and the treatment being effected.

The Formulations

The formulations of the present invention include an effective amount of 1-diphenylmethyl-4-[(2-(4-methylphenyl)-5-methyl-1H-imidazol-4-yl)methyl]piperazine and a suitable amount of an acid for generating a pharmaceutically acceptable salt having a pH above about 3.0 and a solubility above about 4.0 mg/ml. The intravenous formulation optionally includes a suitable tonicifier in a quantity sufficient to achieve isotonicity with body fluids. Other optional pharmaceutically acceptable ingredients, such as stabilizing agents, preservatives, buffers, and the like (all of which are typically commercially available or can be prepared by methods readily known to those skilled in the art) can also be employed. The formulations may include other medicinal and pharmaceutical agents. The balance of the formulation is made up with water.

The intravenous formulations are prepared as solutions incorporating the above-described ingredients within the following approximate ranges:

| Active Agent | 0.1 to 10.0 mg/ml |
| --- | --- |
| Acid | 0.05 to 15.0 mg/ml |
| Tonicifier | none, or q.s. to achieve isotonicity with physiological fluids |
| Water | q.s. to 1 ml |

In a preferred injectable formulation, the ingredients are incorporated within the following approximate ranges:

| Active Agent | 4.0 to 8.0 mg/ml |
| --- | --- |
| Tartaric Acid | 4.03 to 8.05 mg/ml |
| Sorbitol | 35 to 55 mg/ml |
| Water | q.s. to 1 ml |

In the presently preferred formulation, the ingredients are combined as follows:

| Active Agent | 6.0 mg/ml |
| --- | --- |
| Tartaric Acid | 6.19 mg/ml |
| Sorbitol | 40.5 mg/ml |
| Water | q.s. to 1 ml |

The Active Agent

1-Diphenylmethyl-4-[(2-(4-methylphenyl)-5-methyl-1H-imidazol-4-yl)methyl]-piperazine (the "active agent") is made as described in copending applications U.S. Ser. Nos. 042,181, filed Apr. 24, 1987, and 260,969, filed contemporaneously herewith (both previously incorporated by reference).

The Acids

Tartaric acid, citric acid and methane sulphonic acid are all commercially available. They are employed in a molar ratio of about 3 parts of the acid to about one part of the active agent, to generate, in situ, the formation of a pharmaceutically acceptable salt during the formulation process.

The Tonicifiers

Tonicifiers optionally useful in the formulations of the present invention include, e.g., dextrose, potassium chloride, sodium chloride, sorbitol, and manitol, preferably sorbitol.

Other Optional Ingredients

The formulations are water based solutions, and may include other conventional pharmaceutical carriers or excipients, adjuvants, buffers and pH adjusting agents (e.g., NaOH), and in addition, other medicinal and pharmaceutical agents, and the like. For example, in methods of treating stroke, particularly acute ischemic stroke, the active compound can be co-administered with one or more agents active in reducing the risk of stroke, such as aspirin or ticlopidine (preferably ticlopidine, which has been demonstrated to reduce the risk of a second ischemic event).

Preparation

The formulations of the present invention are prepared by placing an amount of acid calculated to generate a pharmaceutically acceptable salt having the desired pH and solubility characteristics into a suitable vessel and dissolving it with water, adding an amount of the active agent sufficient to achieve the desired concentration, adding an amount of tonicifier calculated to render the resulting formulation isotonic with body fluids, adding the amount of water necessary to bring the total volume to the desired concentration, and combining the ingredients. The procedure is carried out from about 15° C. to about 50° C., preferably at about room temperature, and at atmospheric pressure. The resulting formulation is transferred to unit dosage containers (such as bottles or ampoules or prefilled syringes) for storage prior to use.

The formulations can be used as prepared or are administered by preparing a liquid pharmaceutically administerable composition, for example, by dissolving, dispersing, etc. the formulation (prepared as described above) in a carrier, such as, for example, an infusion fluid. Infusion fluids suitable for use with the formulations of the present invention, and demonstrated to be compatible therewith, include: dextrose 5%, sodium chloride 0.9%, dextrose 5%+sodium chloride 0.9%, sodium chloride 0.9%+potassium chloride 0.3%, dextrose 4%+sodium chloride 0.18%+potassium chloride 0.3%, manitol 20%, half strength compound sodium lactate, ringers, darrows, compound sodium lactate, Gentran 40, Gentran 40+sodium chloride 0.9%, and Gentran 70+dextrose 5%.

Actual methods of preparing such dosage forms are known, or will be apparent, to those skilled in this art; for example, see *Remington's Pharmaceutical Sciences,* Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

Administration

1-Diphenylmethyl-4-[(2-(4-methylphenyl)-5-methyl-1H-imidazol-4-yl)methyl]piperazine, is administered at a therapeutically effective dosage, i.e., a dosage sufficient to provide treatment for the disease states previously described. Administration of the formulations of the present invention is by intravenous injection, preferably dispersed in an acceptable infusion fluid, or by other parenteral routes.

Dosage

Generally, a daily dose is from 0.02 to 50 mg/kg of body weight, per day, of the active compound. Most conditions respond to treatment comprising a dosage level on the order of 0.1 to 4 mg/kg of body weight, per day. Thus, for administration to a 70 kg person, the dosage range would be about 1.4 to 3500 mg per day, preferably about 7.0 to 280 mg per day.

UTILITY, TESTING AND ADMINISTRATION

General Utility

The formulations of the present invention are useful for treating mammals having any of a variety of disease states, including:

diseases treated by direct neuronal protection, such as ischemia including focal and global ischemia, spinal injuries, head trauma, and neurological diseases such as Alzheimer's and Huntington's chorea;

diseases treated by inhibition of sodium ion such as uraemic and hyponatraemic encephalopathy; and diseases treated with calcium channel antagonists, including:

- diseases treated by inhibiting cerebrovascular vasospasm and by cerebrovascular vasodilation, such as migraine, stroke, vasospasm due to subarachnoid hemorrhage, epilepsy or epileptic psychotic symptoms, and cerebrovascular ischemia induced by cocaine abuse; and
- cardiovascular diseases, such as hypertension, angina, stable and unstable angina, Prinzmetal angina, arrhythmia, thrombosis, embolism, and congestive heart failure such as chronic or acute cardiac failure; and
- ischemia of lower legs due to peripheral vascular disease, e.g., intermittent claudication;
- spasms of smooth muscle, such as the ureter, the bladder, uterine cramps, diuresis and irritable bowel syndrome; and
- uses during surgery: such as bypass grafts, angiography, angioplasty, organ preservation during transplant, hypertensive crisis or post operative hypertension.

Testing

The efficacy of the active agent is known, as reported in copending applications U.S. Ser. Nos. 042,181, filed Apr. 24, 1987, and 260,969, filed contemporaneously herewith (both previously incorporated herein by reference).

Stability testing of the formulations is done, for example, as described in *Remington's Pharmaceutical Sciences.* "Stability of Pharmaceutical Products," Chapter 81, Mack Publishing Company, Easton, Pa., 15th Ed., 1975. A formulation is prepared and placed in suitable container, storing it at 25° C., and periodically observing the appearance of the samples and removing aliquots to be tested for concentration and pH.

Compatibility with infusion fluids is determined by adding a formulation of the invention to an infusion fluid and inspecting the resulting mixture for formation of any precipitate, discoloration, or the appearance of other physical changes, monitoring the solution active ingredient concentration to ensure no loss in potency, which could lead to decreases in efficacy.

In vivo acceptability is tested by injecting a small amount of the formulation into the tail vein of a rat or other suitable species, for example, as described by Waynforth, *Experimental and Surgical Technique in the Rat*, Chapter 2, pages 42–45 (Academic Press, 1980).

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

This example illustrates the preparation of a representative pharmaceutical formulation containing 1-diphenylmethyl-4-[(2-(4-methylphenyl)-5-methyl-1H-imidazol-4-yl)methyl]piperazine as the active agent.

An injectable preparation is prepared having the following composition:

| Ingredients | | | |
|---|---|---|---|
| Active Agent | 4.0 mg | 4.0 mg | 4.0 mg |
| Tartaric Acid | 4.13 mg | | |
| Citric Acid | | 5.78 mg | |
| Methane Sulphonic Acid | | | 2.64 mg |
| Sorbitol | 45.1 mg | 45.1 mg | 45.1 mg |
| Water | q.s. to 1 ml | q.s. to 1 ml | q.s. to 1 ml |

The acid is added to a vessel and dissolved in water, followed by the addition of the active agent, sorbitol, and water sufficient to bring the total volume to 1 ml.

EXAMPLE 2

This example illustrates the preparation of a preferred pharmaceutical formulation containing 1-diphenylmethyl-4-[(2-(4-methylphenyl)-5-methyl-1H-imidazol-4-yl)methyl]piperazine as the active compound.

An injectable preparation is prepared having the following composition:

| Ingredients | |
|---|---|
| Active Agent | 6.0 mg/ml |
| Tartaric Acid | 6.19 mg/ml |
| Sorbitol | 40.5 mg/ml |
| Water | q.s. to 1 ml |

The acid is added to a vessel and dissolved in water, followed by the addition of the active agent, sorbitol, and water sufficient to bring the total volume to 1 ml.

EXAMPLE 3

Stability Testing

This procedure is a modification of a procedure well known to those skilled in the art, for example, as described in *Remington's Pharmaceutical Sciences*, "Stability of Pharmaceutical Products," Chapter 81, Mack Publishing Company, Easton, Pa., 15th Ed., 1975.

A formulation prepared in accordance with the teachings of Example 2 was transferred to 1 ml glass ampoules and placed in an incubator at 25° C. At periodic intervals, the appearance of the samples was noted, and aliquots were withdrawn and assayed for active agent concentration and pH. The results are reported below:

| Time | Active Agent Content (% LS) | pH | Appearance |
|---|---|---|---|
| 0 | 97.3 | 3.00 | Clear colorless soln. |
| 1 | 97.0 | 3.01 | No change |
| 2 | 97.4 | 3.00 | No change |
| 3 | 98.5 | 2.95 | No change |
| 6 | 96.7 | 2.94 | No change |
| 12 | 96.7 | 2.98 | No change |

The formulations of the present invention show acceptable stability when tested by this method.

EXAMPLE 4

Determination of Irritation Utilizing The Rat Tail Vein Injection

This procedure is a modification of a procedure described by Waynforth in *Experimental and Surgical Technique in the Rat*, Chapter 2, pages 42–45 (Academic Press, 1980). The rat tail vein is dilated by warming, and a test formulation administered by injection, using a 25G needle, with the rat held in a restrainer, and a heat source close enough to keep the tail warm during injection. The tail is observed for signs of irritation, which are outwardly apparent and can be detected by the presence of bruising, swelling, lack of flexibility, lumps, or by observation of distress in the animal upon subsequent administration.

The formulations of the present invention show acceptable levels of irritation when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A pharmaceutical formulation suitable for parenteral administration, comprising a therapeutically effective amount of: 1-diphenylmethyl-4-[(2-(4-methylphenyl)-5-methyl-1H-imidazol-4-yl)methyl]piperazine, tartaric acid, a tonicifier, and water.

2. The formulation of claim 1 where said tonicifier is sorbitol.

3. A pharmaceutical formulation suitable for parenteral administration, comprising:

a therapeutically effective amount of 1-diphenylmethyl-4-[(2-(4-methylphenyl)-5-methyl-1H-imidazol-4-yl)methyl]piperazine, an acid, selected from tartaric acid, citric acid, or methane sulphonic acid, in an amount suitable for generating a pharmaceutically acceptable salt having a pH above about 3.0 and a solubility above about 4.0 mg/ml, optionally, a tonicifier in a quantity of a sufficient to achieve isotonicity with body fluids, and water.

4. The formulation of claim 3 where said acid is tartaric acid.

5. The formulation of claim 3 where said tonicifier is sorbitol.

6. The formulation of claim 4 where said tonicifier is sorbitol.

7. The formulation of claim 3, comprising:

| | |
|---|---|
| Active Agent | 0.1 to 10.0 mg/ml, |
| Acid | 0.05 to 15.0 mg/ml, |
| Tonicifier | none, or q.s. to achieve isotonicity with physiological fluids, and |
| Water | q.s. to 1 ml. |

8. The formulation of claim 3, comprising:

| | |
|---|---|
| Active Agent | 4.0 to 8.0 mg/ml, |
| Tartaric Acid | 4.03 to 8.05 mg/ml, |
| Sorbitol | 35 to 55 mg/ml, and |
| Water | q.s. to 1 ml. |

9. The formulation of claim 3, comprising:

| | |
|---|---|
| Active Agent | 6.0 mg/ml, |
| Tartaric Acid | 6.19 mg/ml, |
| Sorbitol | 40.5 mg/ml, and |
| Water | q.s. to 1 ml. |

10. The formulation of claim 3 including an infusion fluid suitable for intravenous administration.

11. The formulation of claim 10 wherein said infusion fluid is selected from the group consisting of: dextrose 5%, sodium chloride 0.9%, dextrose 5%+sodium chloride 0.9%, sodium chloride 0.9%+potassium chloride 0.3%, dextrose 4%+sodium chloride 0.18%+potassium chloride 0.3%, manitol 20%, half strength compound sodium lactate, ringers, darrows, compound sodium lactate, Gentran 40, Gentran 40+sodium chloride 0.9%, and Gentran 70+dextrose 5%.

12. A method of treating stroke, comprising the parenteral administration of a formulation of claim 3 to a mammal in need thereof.

13. The method of claim 12 wherein said parenteral administration is by intravenous injection.

14. A method of treating stroke, comprising the parenteral administration of a formulation of claim 9 to a mammal in need thereof.

15. The method of claim 14 wherein said parenteral administration is by intravenous injection.

16. A method of producing a stable, soluble physiologically and clinically acceptable solution of 1-diphenylmethyl-4-[(2-(4-methylphenyl)-5-methyl-1H-imidazol-4-yl)methyl]piperazine, suitable for parenteral administration, comprising:

placing a slight molar excess of tartaric acid to a vessel, and dissolving it with water;

adding 1-diphenylmethyl-4-[(2-(4-methylphenyl)-5-methyl-1H-imidazol-4-yl)methyl]piperazine to the vessel, in an amount calculated to give a desired concentration;

adding water in a quantity sufficient to achieve the desired concentration;

thereby generating, in situ, a solution of the tartrate salt of 1-diphenylmethyl-4-[(2-(4-methylphenyl)-5-methyl-1H-imidazol-4-yl)methyl]piperazine.

17. The method of claim 16 further comprising adding an amount of tonicifier suitable to render the resulting solution isotonic with physiological fluids.

* * * * *